US00PP10397P

United States Patent [19]

Trees

[11] Patent Number: Plant 10,397

[45] Date of Patent: May 12, 1998

[54] GERANIUM PLANT NAMED 'BFP-1409 LIGHT SALMON'

[75] Inventor: Scott C. Trees, Arroyo Grande, Calif.

[73] Assignee: Ball Horticultural Company, West Chicago, Ill.

[21] Appl. No.: 697,264

[22] Filed: Aug. 21, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,936 8/1992 Hanes ..... Plt./87.12

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

The new and distinct Pelargonium ×hortorum cultivar named 'BFP-1409 Light Salmon'is provided. This new Zonal Geranium was the result of a controlled breeding program wherein a plant designated 5076-16 (non-patented in the United States) was pollinated by a plant designated 4123C (non-patented in the United States). The new cultivar forms attractive semi-double salmon florets. Medium green foliage with slight zonation is well retained during shipment. The growth habit is vigorous self-branching and does not require the use of a growth regulator.

1 Drawing Sheet

SUMMARY OF THE INVENTION

The present invention comprises a new and distinct Geranium cultivar, botanically known as *Pelargonium ×hortorum* Bailey, and hereinafter is referred to by the cultivar name 'BFP-1409 Light Salmon'.

The new cultivar is a product of a planned breeding program which had the objective of the creation of a Geranium cultivar that exhibits uniform flowers, medium green foliage, a vigorous self-branching growth habit that requires no growth regulator, a propensity for rapid rooting, and stable foliage coloration during shipment.

The breeding program that resulted in the production of the new cultivar of the present invention was carried out in a controlled environment during 1992 at Arroyo Grande, Calif. U.S.A. The female parent (i.e., seed parent) was a plant designated 5076-16(non-patented in the United States) which exhibits semi-double salmon florets with dark green foliage. The male parent (i.e., pollen parent) was a plant designated 4123C (non-patented in the United States) which exhibits single cameo florets with dark green foliage. The parentage of the new 'BFP-1409 Light Salmon' cultivar can be summarized as follows:

5076-16×4123C.

'BFP-1409 Light Salmon' was discovered and selected during 1993 as a highly distinctive flowering plant from among the progeny of the stated cross at Arroyo Grande, Calif. U.S.A. This plant was intially designated BFP-1409.

It was found that the new cultivar of the present invention:

(a) exhibits attractive semi-double salmon florets,
(b) forms attractive medium green foliage with slight zonation, and
(c) exhibits a medium self-branching growth habit in the absence of a growth regulator.

After senescence the flowers abscise and drop. To date, observations of the new 'BFP-1409 Light Salmon' cultivar have not demonstrated resistance to Botrytis or any other specific disease.

The first act of asexual reproduction of the 'BFP-1409 Light Salmon' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demostrated that the combination of unique characteristics as herein described for the 'BFP-1409 Light Salmon'cultivar is fixed and is retained through successive generations of such asexual reproduction.

The new 'BFP-1409 Light Salmon' cultivar has not been observed under all possible environmental conditions. Accordingly, the described phenotype may vary somewhat with variations in the environment, such as temperature, light intensity, and day length.

Of the many commerical cultivars the 'American Light Salmon' cultivar (U.S. Plant Pat. No. 7,936) is considered to be the most similar to the new cultivar of the present invention. When the new cultivar of the present invention is compared to the 'Americana Light Salmon' cultivar, it is found that the 'BFP-1409 Light Salmon' cultivar exhibits umbels of a smaller diameter (e.g., approximately 8.5 to 9.5 cm. vs approximately 10.5 to 11.2 cm.), shorter peduncles (e.g., approximately 11 to 12 cm. vs. approximately 17.5 to 18 cm.), and more umbels per plant (e.g., approximately 4 to 6 vs. approximately 3 to 4).

The new cultivar of the present invention is being marketed under the Designer trademark.

BRIEF DESCRIPTION OF THE PHOTOGRAPH

The accompanying photograph shows the new 'BFP-1409 Light Salmon'cultivar with colors being as nearly true as it is reasonably possible to make the same in a color illustration of this character. The plant was being grown in a greenhouse at West Chicago, Ill., U.S.A. The general appearance of the overall plant including the flower and foliage charcteristics is illustrated.

DETAILED DESCRIPTION

The following observations, measurements and comparisons describe plants grown in greenhouses located at West Chicago, Ill., U.S.A., under conditions which approximate those generally used in commercial practice. In the following description, color references are made to the R.H.S. Colour Chart of The Royal Horticultural Society, London, England. The color values were determined on September 22nd, under natural light conditions of 200 footcandles.

Classification:

*Botanical.—Pelargonium×hortourm* Bailey, cv. 'BFP-1409 Sight Salmon'.

Commerical.—Zonal Geranium.

Inflorescence

A. Umbel:

*Average diameter.*—Approximately 8.5 to 9.5 cm. compared to approximately 10.5 to 11.2 cm. for the 'American Light Salmon' cultivar.

*Average depth.*—Approximately 6.5 to 7.5 cm. compared to approximately 5.3 to 7 cm. for the 'Americana Light Salmon'cultivar.

*Peduncle length*—Approximately 11 to 12 cm. compared to approximately 17.5 to 18 cm. for the 'Americana Light Salmon'cultivar.

*Pedicel length.*—Approximately 2.5 to 3.5 cm. compared to approximately 2.9 to 3.3 cm. for the 'Americana Light Salmon' cultivar.

*Number of umbels plant.*—When grown in a 10 cm. pot at 9 weeks after the sticking of a rooted cutting, there commonly are approximately 4 to 6 umbels per plant. The 'Americana Light Salmon'cultivar also commonly forms approcimately 3 to 4 umbels per plant.

*Number of florets/umbel.*—When grown in 10 cm. pots at 9 weeks, approximately 25 to 33 florets per umbel commonly are formed. This compares to approximately 30 to 35 florets per umbel for the 'Americana Light Salmon' cultivar under the same growing conditions.

B. Corolla:

*Buds.* —Elliptical to round in configuration, initially light pink, Red Group 49C, and changing to darker pink, Red Group 50D, at the time of opening, and approximately 10 to 11 mm. in length and approximately 6.5 to 7 mm. in width. The buds tend to commonly face outward and downward before they open.

*Pedicels.* —*Commonly approximately* 2.5 to 3.5 cm. in length.

*Average diameter*—Approximately 4.5 to 5 cm. for both the 'BFP-1409 Light Salmon'and the 'Americana Light Salmon' cultivars.

*Form* —Both the 'BFP-1409 Light Salmon' cultivar and the 'Americana Light Salmon' cultivar are semi-double with petaloids.

*Petals.* —Spatulate shaped, dull in appearance, and somewhat rippled. Commonly approximately 5 to 6 petals are present per floret. This compares to approximately 7 petals per floret for the 'Americana Light Salmon' cultivar.

*Number of petaloids.*—Commonly forms 1 to 2 petaloids per floret wheras the 'Americana Light Salmon' cultivar commonly forms 2 to 4 petaloids per floret.

*Color.* —General tonality from a distance of three meters: Light salmon. Adaxial; The distal one-third is Red Group 50D, and the proximal two thirds is Red Group 50C with veins of Red Group 50B. This compares to Red-Purple Group 62D at the distal edge and Red Group 50B at the base for the 'Americana Light Salmon'cultivar. Abaxial: Red Group 56D with veins of Red Group 49C. This compares to Red-Purple Group 62D for the 'Americana Light Salmon' cultivar.

C. Reproductive organs:

*Androecium.*—The anthers are commonly approximately 1.5 mm. in length. The pollen color is Orange-Red Group 32A. This compares to Orange-Red Group 31A for the 'Americana Light Salmon' cultivar. The filaments are approximately 4 to 7 mm. in length.

*Gynoecium.* —The pistil length commonly is approximately 10 mm. There is a single stigma which commonly has a length of approximately 5 mm. which commonly branches into 5 parts, the ovary is approximately 2 mm. in length, and the style length is approximately 3 mm.

*Fertility.* —Commonly does not produce fruits in the absence of mechanical fertilization.

D. Spring flowering response period: Approximately 6 to 7 weeks from rooted cuttings under greenhouse conditions.

E. Outdoor flower production: Freely flowering under outdoor growing conditions with substantially continuous blooming.

F. Durability: Ships well.

Foliage: Medium green with slight zonation. The leaves are thick and pilose. The rib and vein pattern is palmate.

*Form.*—Renform, with a cordate base.

*Margin.*—Bi-crenate and somewhat undulate.

*Color.—Adaxial: Yellow-Green group* 147A with the outer edge being slightly darker than Yellow-Green Group 147A. This compares to Yellow- Green Group 146B at the center and Yellow-Green Group 146A at the outer edge for the 'Americana Light Salmon' cultivar. Abaxial: Yellow-Green Group 147B. This compares to Yellow-Green Group 147C for the 'Americana Light Salmon' cultivar.

*Size.*—Approximately 9.3 to 9.7 cm. in width at the widest point and approximately 8.2 to 8.9 cm.in length. This compares to approximately 9.2 to 9.5cm. in width at the widest point and approximately 8 to 8.5 cm in length for the 'Americana Light Salmon' cultivar.

*Petioles.*—Commonly approximately 2.7 to 5.7 cm. in length. This compares to a length of approximately 3.0 to 5.5 cm. for the 'Americana Light Salmon' cultivar.

B. General appearance and form:

*Internode length.* —Commonly varies from approximately 1.8 to 2.2 cm. This compares to approximately 2 to 2.8 cm. for the 'Americana Light Salmon' cultivar.

*Branching pattern.*—Freely basal branching. No pinching is required to obtain self-branching. A vigorous self-branching growth habit is observered in the absence of a growth regulator.

*Height.* —Approximately 18 to 22 cm. above a 10 cm. pot at 9 weeks under standard greenhouse conditions. This compares to approximately 22 to 24 cm. for the 'American Light Salmon' cultivar.

I claim:

1. A new and distinct cultivar Geranium plant named 'BFP-1409 Light Salmon', substantially as kerein shown and described, which:

(a) exhibits attractive semi-double salmon florets,
(b) forms attractive medium green foliage with slight zonation, and
(c) exhibits a vigorous self-branching growth habit in the absence of the use of a growth regulator.

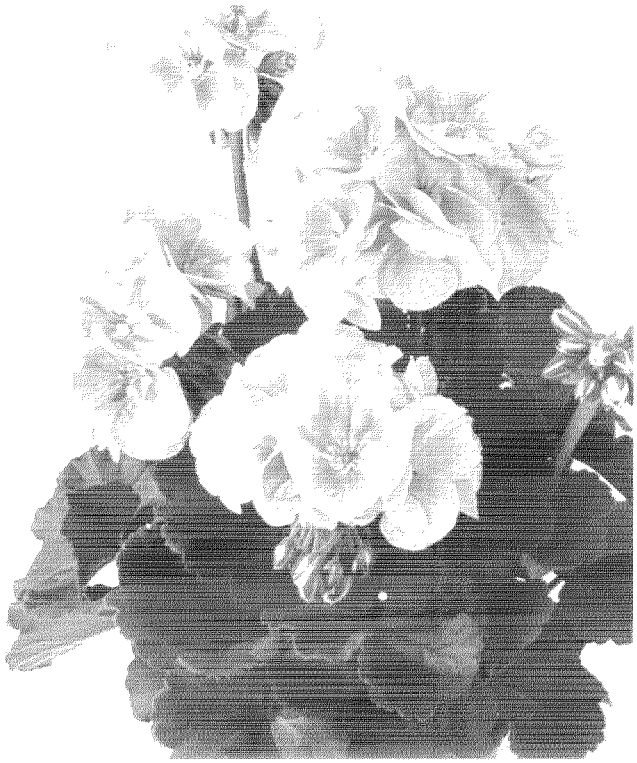

* * * * *